May 30, 1972 L. B. SHERRILL Plant Pat. 3,199
PEACH TREE
Filed Dec. 17, 1970
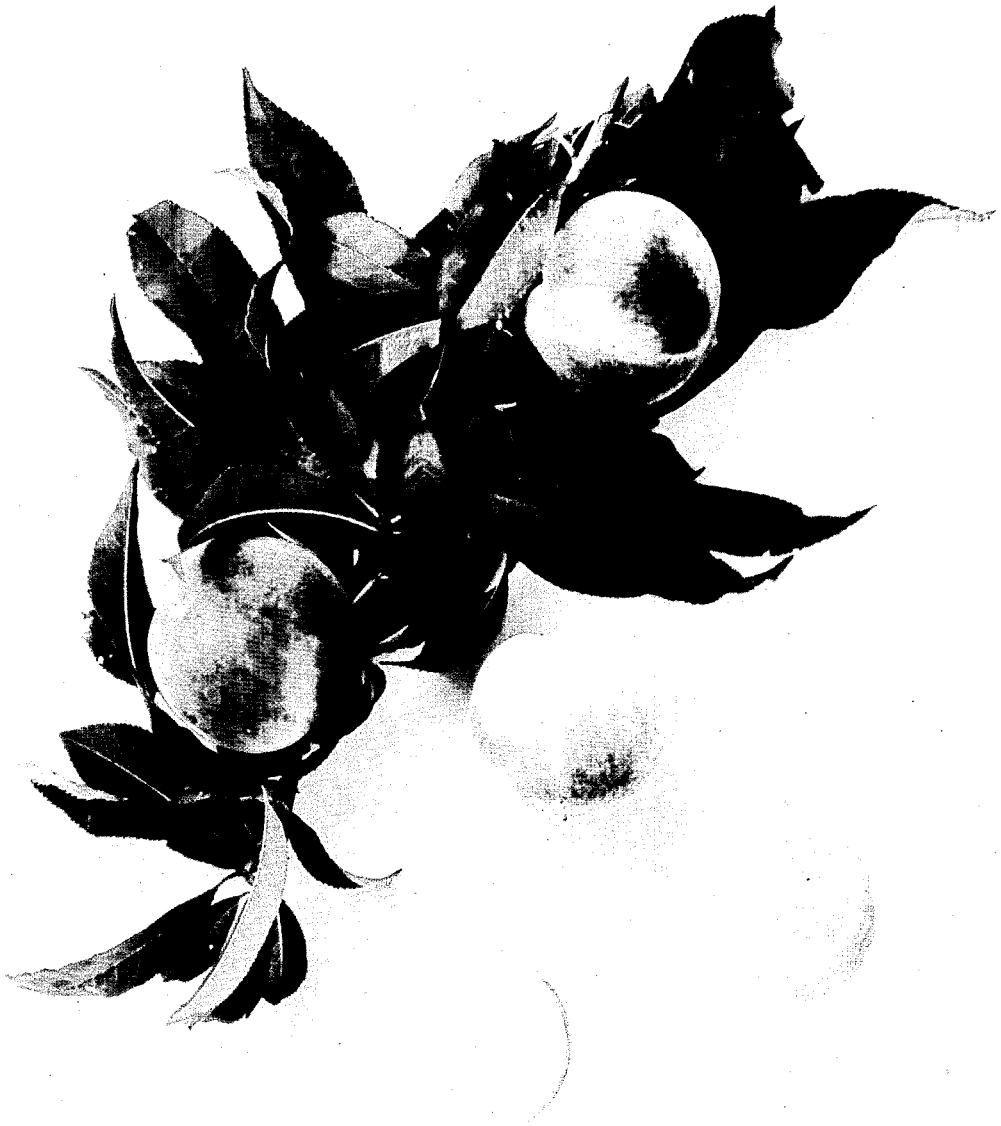
INVENTOR
Lewis B. Sherrill
BY
Webster & Webster
ATTORNEYS

United States Patent Office

Plant Pat. 3,199
Patented May 30, 1972

3,199
PEACH TREE

Lewis B. Sherrill, Bakersfield, Calif., assignor to Patterson & Hale, Bakersfield, Calif.

Filed Dec. 17, 1970, Ser. No. 99,329
Int. Cl. A01h 5/03
U.S. Cl. Plt.—43 1 Claim

ABSTRACT OF THE DISCLOSURE

A peach tree of medium size, medium vigor, spreading growth, vase form, hardy for California peach-producing areas, and a regular and very productive bearer of early ripening, large, uniform, globose, semi-clingstone fruit having firm yellow flesh and yellow skin overspread to a substantial extent with red.

*Origin of the variety*

The present variety of peach tree was discovered by me as a single branch sport on a Merrill Beauty (United States Plant Patent No. 905) peach tree growing in an orchard on a ranch in Kern County, Calif.; such orchard being under my supervision. When such limb sport bore fruit, the characteristics thereof (as hereinafter described) were recognized by me as new and distinct, and I, therefore, undertook asexual reproduction of the variety.

*Asexual reproduction of the variety*

I asexually reproduced the present variety of peach tree by removing dormant scions from the original limb sport and grafting such scions into an older peach tree in my experimental orchard also located in Kern County, Calif. Such asexual reproductions, upon bearing fruit, ran true to the original limb sport in all respects.

*Summary of the variety*

The herein claimed variety of peach tree is of medium size, medium vigor, spreading growth, vase form, hardy for California peach-producing areas, and a regular and very productive bearer of early ripening, large, uniform, globose, semi-clingstone fruit having firm yellow flesh and yellow skin overspread to a substantial extent with red; the variety being particularly characterized—as to novelty, and in comparison to other peach varieties maturing in the same season—by fruit which is of larger size, firmer flesh, a more brilliant exterior color, and a superior flavor. These characteristics make the fruit of the present variety advantageously distinctive for the fresh fruit market, and especially desirable for dessert use. Other varieties maturing in the same season, and as to which the present comparison is made, include Early Coronet (United States Plant Patent No. 2,336), Robin (United States Plant Patent No. 529), and Cardinal (U.S.D.A.).

*Brief description of the drawing*

The drawing is an illustration, by photographic reproduction in color, of a twig with attached fruit, and other fruit detached; one of the latter being cut chordally to expose the flesh to view.

*Description of the variety*

The botanical details of this new and distinct variety of peach tree—with color definitions (except those in common color terms) referenced to Maerz and Paul Dictionary of Color—are as follows:

Tree:
- *Size.*—Medium.
- *Vigor.*—Medium.

- *Growth.*—Spreading.
- *Form.*—Vase-formed.
- *Hardiness.*—Hardy for California peach-producing areas.
- *Production.*—Excellent.
- *Bearing.*—Regular.

Trunk:
- *Size.*—Medium stocky.
- *Texture.*—Medium.

Branches:
- *Size.*—Medium stocky.
- *Texture.*—Medium.
- *Color.*—Brown.
- *Surface.*—Dull.
- *Lenticels.*—Number—few. Size—small, unevenly spaced.

Leaves:
- *Size.*—The vigorous growth is expressed in large uniform leaves; average length (mature leaves)—7½"; average width (mature leaves)—1⅝".
- *Form.*—Lanceolate.
- *Thickness.*—Medium.
- *Margin.*—Evenly crenate.
- *Petiole.*—Medium size; average length—½".
- *Glands.*—Average number—2; Reniform; Small to medium; Positioned opposite on petiole, adjacent blade; Light green to yellow.
- *Stipules.*—None.
- *Color.*—Top side—Glossy dark green (22–L–9). Under Side—Lighter dull green (21–K–8) with no pubescence.

Flower buds:
- *Hardiness.*—The buds are hardy for California peach-producing areas. Dormancy requirements are 750 hours chilling below 45° F.
- *Form.*—Plump, slightly pointed at the apex.
- *Color.*—Light pink.

Flowers:
- *Blooming period.*—Date of first bloom—Average—March 2nd, coinciding with most commercial peach varieties.
- *Type.*—Showy, petals open flat.
- *Color.*—Light pink, with base of each petal deep red to maroon.

Fruit:
- *Maturity when described.*—Firm ripe.
- *Date of first picking.*—May 28, 1970.
- *Date of last picking.*—June 4, 1970.
- *Size.*—Large—larger than other peach varieties maturing in the same season; uniform over entire bearing area of the tree; average diameter axially—2⅜"; average transverse diameter—2⅜".
- *Form.*—Globose, with slight depression over the suture.
- *Suture.*—Distinct from base to apex. Overlaid with a narrow but distinct yellow pigment. Slightly depressed, with depression extending beyond pistil point.
- *Ventral surface.*—Uniformly rounded.
- *Cavity.*—Uniformly flared, with slight elongation at the suture.
- *Base.*—Rounded.
- *Apex.*—Uniformly rounded.
- *Pistil point.*—Slight.

Skin:
- *Tendency to crack.*—None.
- *Color.*—Yellow (9–L–5) substantially overspread with red (6–L–5), mottled and streaked near the pistil point. Skin color in the stem cavity—yellow to greenish at the stem. Overall color effect—brilliant.

Flesh:

*Amygdalin.*—Slight.

*Juice.*—Moderate.

*Texture.*—Medium; melting.

*Fibers.*—Abundant; tender.

*Ripens.*—Evenly; cavity area last to attain maturity.

*Flavor.*—Subacid; distinctly peach.

*Aroma.*—Distinct.

*Eating quality.*—Excellent in comparison to other peach varieties maturing in the same season.

*Color.*—Light yellow (10–L–5). Surface of pit cavity—Light yelow. Fibers extending from pit cavity into flesh are slightly lighter yellow than the flesh.

Stone:

*Type.*—Semi-clingstone. Adheres on all surfaces when fruit is firm ripe. When fruit is soft ripe, stone is free except along the dorsal and ventral edges.

*Size.*—Medium; average length—1¼"; average breadth—⅞"; average thickness—⅝".

*Form.*—Oblong; sharp pistil point; irregularly cunate at apex.

*Hilum.*—Oblong; narrowly indented.

*Apex.*—Acuminate; very sharp point.

*Sides.*—Unequal.

*Surface.*—Irregularly furrowed and pitted.

*Ridges.*—Interrupted both sides.

*Ventral edge.*—Thin; irregular; fading at apex.

*Dorsal edge.*—Pronounced; unevenly cunate near apex.

*Tendency to split.*—None.

*Pits.*—Dark brown; not matured.

*Fertility.*—Self-fertile.

*Color.*—Tan (11–K–6).

Use: Dessert; fresh fruit shipping.

Shipping and keeping quality:

Good; packed firm ripe, the fruit matures to maximum eating quality with retention of excellent appearance at terminal markets.

The peach tree and its fruit herein described may vary in slight detail due to climatic and soil conditions under which the variety may be grown; the present description being of the variety as grown in the Central Valley of California.

I claim:

1. A new and distinct variety of peach tree, substantially as illustrated and described, which is of medium size, medium vigor, spreading growth, vase form, hardy for California peach-producing areas, and a regular and very productive bearer of early ripening, large, uniform, globose, semi-clingstone fruit having firm yellow flesh and yellow skin overspread to a substantial extent with red; the variety being particularly characterized, in comparison to other peach varieties maturing in the same season, including Early Coronet, Robin, and Cardinal, by fruit which is of larger size, firmer flesh, a more brilliant overall color effect, and a superior flavor.

No references cited.

ROBERT E. BAGWILL, Primary Examiner